United States Patent [19]

Yamada et al.

[11] 4,269,942
[45] May 26, 1981

[54] PROCESS FOR PREPARING ACYL-COA SYNTHETASE LCF-18

[75] Inventors: Hideaki Yamada; Sakayu Shimizu; Yoshiki Tani, all of Kyoto, Japan

[73] Assignee: Amano Pharmaceutical Co. Ltd., Nagoya, Japan

[21] Appl. No.: 132,177

[22] Filed: Mar. 20, 1980

Related U.S. Application Data

[63] Continuation-in-part of Ser. No. 28,604, Apr. 9, 1979, Pat. No. 4,229,538.

[30] Foreign Application Priority Data

May 15, 1978 [JP] Japan ............................. 53-056604
Jan. 26, 1979 [JP] Japan ............................. 54-007244

[51] Int. Cl.³ ............................................... C12N 9/10
[52] U.S. Cl. ..................................... 435/193; 435/15; 435/875
[58] Field of Search ......................... 435/193, 15, 875

[56] References Cited

PUBLICATIONS

Samuel et al., Eur. J. Biochem., vol. 12, (1970), 576–582.
Ray et al., Proc. Natl. Acad. Sci., vol. 73, No. 12, pp. 4374–4378, Dec. 1976.
Kamiryo et al., Proc. Natl. Acad. Sci, vol. 74, No. 11, pp. 4947–4950, Nov. 1977.

Primary Examiner—Lionel M. Shapiro
Attorney, Agent, or Firm—Browdy & Neimark

[57] ABSTRACT

Acyl-CoA synthetase, having a high activity to $C_{16}$–$C_{18}$ long chain fatty acids, is obtained by cultivating *Pseudomonas aeruginosa* IFO 3919. *Pseudomonas aeruginosa* IFO 3919 can produce acyl-CoA synthetase LCF-18 in large quantities, and the acyl-CoA synthetase LCF-18 produced by *Pseudomonas aeruginosa* IFO 3919 is very stable in storage.

1 Claim, 4 Drawing Figures

PROCESS FOR PREPARING ACYL-COA SYNTHETASE LCF-18

CROSS-REFERENCE TO RELATED APPLICATIONS

The present application is a continuation-in-part of application Ser. No. 028,604, filed Apr. 9, 1979, now U.S. Pat. No. 4,229,538, issued Oct. 21, 1980, the entire contents of which are hereby incorporated by reference.

FIELD OF THE INVENTION

The present invention relates to a method for the production of acyl-CoA synthetase from microorganisms, and more particularly, the present invention is concerned with a fermentative production of acyl-CoA synthetase by *Pseudomonas aeruginosa* IFO 3919, the enzyme having a high activity to $C_6$–$C_{19}$ fatty acids, more particularly to $C_{16}$–$C_{18}$ long chain fatty acids.

BACKGROUND OF THE INVENTION

In general, acyl-CoA synthetase is an enzyme which thioesterifies non-esterified fatty acid in the presence of CoA, ATP and Mg ion to make acyl-CoA, and it is also called thiokinase. This enzymatic reaction proceeds as follows:

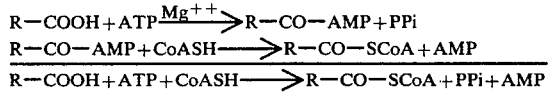

$$R-COOH+ATP \xrightarrow{Mg^{++}} R-CO-AMP+PPi$$
$$R-CO-AMP+CoASH \longrightarrow R-CO-SCoA+AMP$$
$$R-COOH+ATP+CoASH \longrightarrow R-CO-SCoA+PPi+AMP$$

In recent years, with the discovery of the physiological significance of non-esterified fatty acid in vivo, an increase or decrease of the amount of serum non-esterified fatty acid has come to be medically regarded as important. For example, it has been found that an extreme increase of serum non-esterified fatty acid is recognized in the case of the disease of diabetes.

As a result, an increase of serum non-esterified fatty acid, detected by its determination, has come to be utilized for the diagnosis of the condition of such a disease as diabetes, but the serum non-esterified fatty acid has been generally determined by chemical colorimetric method. But the chemical colorimetric method requires a large quantity of blood, complicated analytical procedures and a longer time to perform it, resulting in this method being undesirable. Then, with the recent development of the method for clinical laboratory use, the quantitative determination method of non-esterified fatty acid by so-called enzymatic method has recently come to be used.

In order to quantitatively determine non-esterified fatty acid according to the enzymatic method, non-esterified fatty acid and acyl-CoA synthetase are reached to form acyl-CoA and the product formed by this reaction is enzymatically determined, thereby obtaining the concentration of non-esterified fatty acid. But with respect to the serum non-esterified fatty acid, since $C_{16}$–$C_{18}$ long chain fatty acids are contained in large quantities in serum, an acyl-CoA synthetase that is able to thioesterify efficiently $C_{16}$–$C_{18}$ long chain fatty acids to make acyl-CoA is naturally required. However, the acyl-CoA synthetase derived from liver microsome of rat is the only one known which is fit for this purpose.

However, as this acyl-CoA synthetase is derived from an animal, it is very expensive; therefore, for economic reasons it has been desired to derive the acyl-CoA synthetase from microorganisms, which is not an expensive origin.

Heretofore, as the microorganisms being able to produce acyl-CoA synthetase, the following is known:

*Escherichia coli* [European Journal of Biochemistry, vol. 12, 576–582 (1970)]; *Bacillus megaterium* strain M [Biochemistry, vol. 4, 85–95 (1965)]; Torulopsis $Y_8$ [Journal of Bacteriology, vol. 104, 1397–1398 (1970)]; Pseudomonas 22 [Journal of Bacteriology, vol. 105, 1216–1218 (1971)] and *Nocardia asteroides* [Journal of Bacteriology, vol. 114, 249–256 (1973)].

But since all of these known strains produce, as substrate specificity, such an acyl-CoA synthetase that has an optimum activity to the fatty acids having fourteen and less carbon atoms in the carbon chain, such enzyme derived from these strains cannot be employed for clinical laboratory determination of $C_{16}$–$C_{18}$ long chain fatty acids.

SUMMARY OF THE INVENTION

With respect to the acyl-CoA synthetase which acts on $C_{16}$–$C_{18}$ long chain fatty acids as strongly as that derived from rat liver microsome, if such a strain that produces said acyl-CoA synthetase in large quantities can be found among the enzyme producing microorganisms, there should able to be great industrial usefulness, and, from this point of view, the inventors of the present invention have pursued their studies and, as a result, it was discovered that *Pseudomonas aeruginosa* IFO 3919 can produce such enzyme in large quantities, and the acyl-CoA synthetase produced by *Pseudomonas aeruginosa* IFO 3919 is very stable in storage, and thus completed the present invention.

BRIEF DESCRIPTION OF THE DRAWINGS

In FIG. 3, in case of pH values from 6.0 to 8.0 and from 7.5 to 9.0, potassium phosphate buffer and Tris-HCl buffer were respectively used.

DETAILED DESCRIPTION OF PREFERRED EMBODIMENTS

Figure 1:
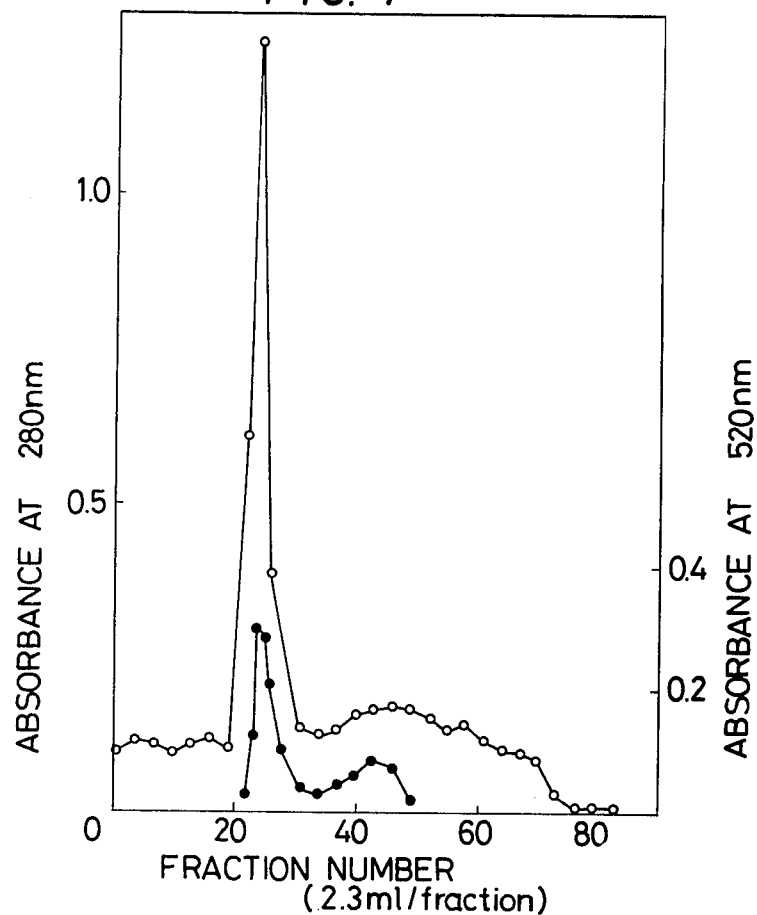
FIG. 1 is a pattern showing the partial purification of the present enzyme by Sephadex G-200 treatment.
Figure 3:
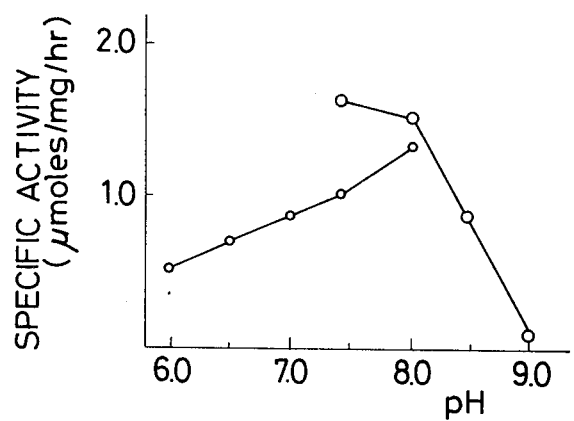
FIG. 3 and FIG. 4 are graphs showing the optimum pH and optimum temperature of the present enzyme.
Figure 2:
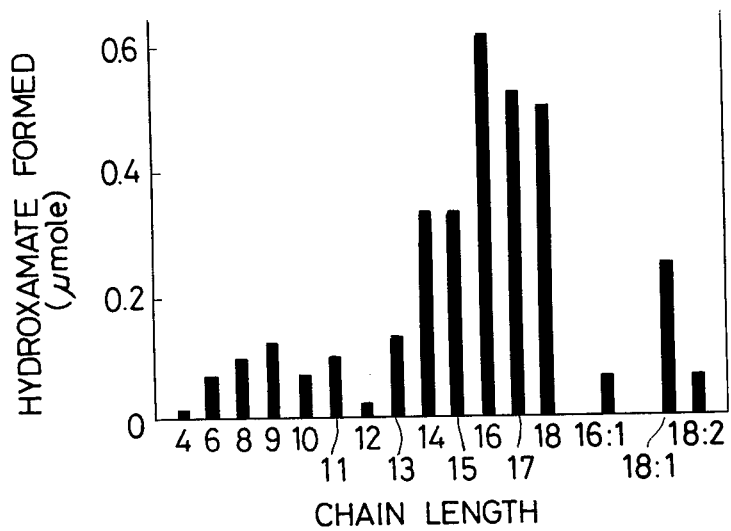
FIG. 2 is a pattern showing the substrate specificity of the present enzyme against each fatty acid having various carbon chain lengths.
Figure 4:
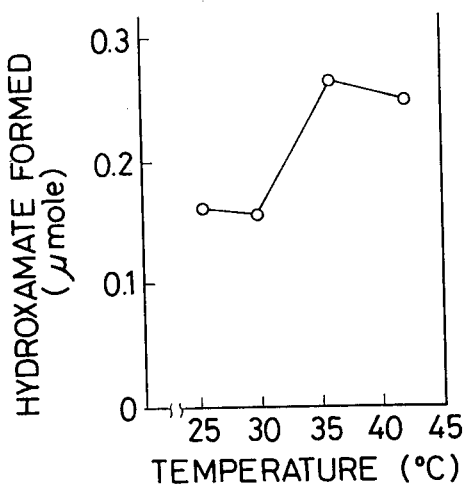

*Pseudomonas aeruginosa* IFo 3919 is stored in IFO (Institute for Fermentation, Osaka), open to the public and freely available.

As a medium to be used, both natural media and synthetic media, containing sources of carbon, nitrogen and inorganic salts and sources of other nutrients in addition, can be widely used. As sources of carbon, the following can be used: $C_4$ to $C_{18}$ fatty acids, for example oleic acid, palmitic acid, linoleic acid, etc., and salts thereof, for example: sodium salt, potassium salt, etc., as well as such as glucose, fructose, galactose, glycerol, succinate, citrate, sorbitol or any other commonly used carbon source.

As sources of nitrogen, the following can be used: inorganic nitrogen compounds such as sodium nitrate, ammonium sulfate, ammonium chloride, etc., or organic nitrogen compounds such as peptone, meat extract, corn steep liquor, yeast extract, etc. As inorganic salts, KH$_2$PO$_4$, MgSO$_4$, etc., can be used, and in addition to this, Triton K-100 is used as surface active agent.

A preferred composition of the medium to carry out the present invention is exemplified by the following: sodium palmitate 1.0% or succinate 0.5%; peptone 0.3%; K$_2$HPO$_4$ 0.1%, yeast extract 0.03% and MgSO$_4$·7H$_2$O 0.05%. As culturing conditions, the strain may be advantageously cultured at 22°–37° C. for 1–3 days under aerobic conditions.

The fermentation broth thus obtained is centrifuged or filtered at reduced pressure to obtain cells. The cells thus obtained are disrupted by ultrasonic oscillator (6 minutes at 15° C. and below), and moreover, they are subjected to a centrifugal separation to obtain supernatant. Then from the supernatant, acyl-CoA synthetase is purified according to the following procedure. First of all, the supernatant, namely crude enzyme solution, is fractionated with ammonium sulfate (30–45% saturation), then it is applied to a Sephadex G-200 column, and furthermore the active fractions are fractionated by 30–50% saturation with ammonium sulfate, and then are subjected to DEAE-cellulose and Sephadex G-200 treatments, so that acyl-CoA synthetase is obtained. Physical and chemical properties of acyl-CoA synthetase thus obtained are as follows:

1. Substrate specificity:

This enzyme acts on C$_6$–C$_{19}$ carbon chain fatty acids, especially on C$_{16}$–C$_{18}$ long chain fatty acids to produce respectively acyl-CoA synthetase according to the used fatty acid.

2. Optimum pH:

The optimum pH of the present enzyme is near 7–8.

3. Optimum temperature:

The optimum temperature of the present enzyme is 35°–45° C.

4. Stability:

The present enzyme is stable in the solution (pH 7.4) of 0.02 M Tris-HCl buffer, containing 10 mM 2-mercaptoethanol at 5° C. and below for 7 days, and furthermore, it is stable for 1 month and more in the presence of glycerol at final concentration of 50%.

5. Effect of Inhibitor, etc.

A high concentration of water-soluble long chain fatty acid, such as lauric acid, oleic acid, palmitooleic acid, etc., inhibits the reaction extremely. But this inhibitory action is reduced in case of coexistence of serum albumin.

Yields and stabilities of each acyl-CoA synthetase produced by using *Pseudomonas aeruginosa* IFO 3919 and other microorganisms are shown in Table 1.

TABLE 1

| Micro-organism | Used medium | Yield C$_{16}$—CoA synthetase activity ($\mu$ mol/mg/hr) $\times$ 10$^3$ | Stability Remaining specific activity after storage (0°~4° C.) for 7 days in | |
|---|---|---|---|---|
| | | | 0.01M KPB (pH7) | 0.01M KPB (pH7) + 15% glycerol |
| *Escherichia intermedia* IFO 13545 | Glucose | <2 | — | — |
| | Palmitate | 41.1 | 6.5 | 12.1 |
| *Escherichia coli* IFO 13168 | Glucose | <2 | — | — |
| | Palmitate | 14.9 | <2 | 5.6 |
| *Escherichia coli* IFO 3701 | Glucose | <2 | — | — |
| | Palmitate | 19.6 | 3.7 | 6.5 |
| *Candida lipolytica* IFO 0717 | Glucose | 40.2 | 6.5 | 18.7 |
| | Palmitate | 115.0 | 9.3 | 26.1 |
| *Candida lipolytica* IFO 1195 | Glucose | 18.7 | 2.8 | 4.6 |
| | Palmitate | 14.9 | 3.7 | 5.6 |
| *Pseudomonas aeruginosa* IFO 3445 | Glucose | 68.2 | 40.2 | 47.6 |
| | Palmitate | 112.2 | 65.4 | 81.3 |
| *Pseudomonas aeruginosa* IFO 3456 | Glucose | 36.4 | 16.8 | 28.0 |
| | Palmitate | 33.6 | 16.8 | 28.9 |
| *Pseudomonas aeruginosa* IFO 3919 | Glucose | 68.2 | 30.8 | 47.6 |
| | Palmitate | 125.2 | 83.2 | 93.5 |
| *Enterobacter aerogenes* IFO 12010 | Glucose | <2 | — | — |
| | Palmitate | 8.4 | <2 | 2.8 |
| *Serratia marcescens* IFO 3054 | Glucose | 4.6 | — | — |
| | Palmitate | 59.8 | 4.6 | 14 |
| *Proteus mirabilis* IFO 3849 | Glucose | <2 | — | — |
| | Palmitate | 24.3 | 4.6 | 5.6 |
| *Aeromonas hydrophilia* IFO 3820 | Glucose | 18.7 | 4.6 | 12 |
| | Palmitate | 53.2 | 9.3 | 28.9 |
| *Aspergillus sojae* IFO 4386 | Glucose | 24.3 | <2 | 4.6 |
| | Palmitate | 30.8 | <2 | 4.6 |
| *Penicillium chrysogenum* IFO 4626 | Glucose | 14.0 | <2 | <2 |
| | Palmitate | 63.5 | <2 | <2 |
| *Fusarium lini* IFO 5880 | Glucose | 28.0 | <2 | <2 |
| | Palmitate | 47.6 | <2 | <2 |
| *Gibberella fujikuroi* IFO 5268 | Glucose | 49.5 | <2 | <2 |
| | Palmitate | 62.6 | <2 | <2 |
| *Hansenula fabianii* IFO 1370 | Glucose | 4.6 | — | — |
| | Palmitate | 2.8 | — | — |
| *Torulopsis candida* IFO 0380 | Glucose | 9.3 | <2 | 2.8 |
| | Palmitate | 6.5 | <2 | 2.8 |

KPB: Potassium phosphate buffer
—: Not determined

Activity of the present enzyme was determined in accordance with the method of Kornberg-Pricon [Journal of Biological Chemistry, vol. 204, 329–343 (1953)] by using long chain fatty acids, such as palmitate (C$_{16}$) or myristate (C$_{18}$) as substrate.

An activity (specific activity) is represented by the amount of hydroxamate ($\mu$mole) which is produced by 1 mg of enzyme protein per hour.

Acyl-CoA synthetase obtained according to the present invention has a characteristic of acting on C$_{16}$–C$_{18}$ long chain fatty acids just as the acyl-CoA synthetase derived from rat liver microsome. This is the first time that such acyl-CoA synthetase has even been discovered from microorganisms, so the acyl-CoA synthetase according to the present invention is called acyl-CoA synthetase LCF-18.

Acyl-CoA synthetase LCF-18 is obtained from microorganisms, therefore it is possible to produce it on a large industrial scale, and since it has strong activity to $C_{16}$–$C_{18}$ long chain fatty acids, it is extremely useful for the determination of human serum non-esterified fatty acid.

The quantitative determination method of serum non-esterified fatty acid by employing acyl-CoA synthetase LCF-18 is as follows:

Reacting acyl-CoA synthetase LCF-18 with serum non-esterified fatty acid in the presence of ATP and CoA, reacting myokinase with thus formed AMP in the presence of ATP, reacting pyruvate kinase with thus formed ADP in the presence of phosphoenol-pyruvate, and then reacting lactate dehydrogenase with thus formed pyruvate in the presence of NADH, and in consequence NADH being allowed to change into NAD, then the concentration of the resultant reduced NADH is measured at 340 nm. This reaction may be illustrated by the following equations (1) to (4):

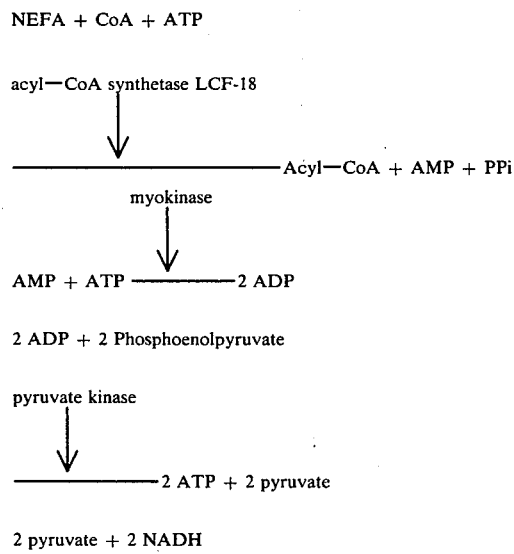

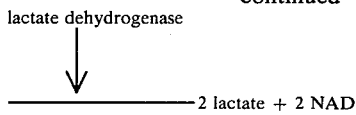

According to the present method, the accurate quantitative determination of serum non-esterified fatty acid can be performed, and the diagnosis of diabetes, etc., can be easily performed.

Next, the present invention is described in the following example:

500 ml Sakaguchi flasks each containing 200 ml of a main medium are prepared. The main medium (10l, pH 6.4) is composed of 0.5% of succinate, 0.3% of peptone, 0.1% of $K_2HPO_4$, 0.03% of yeast extract and 0.05% of $MgSO_4.7H_2O$, and it is sterilized for 20 minutes at 120° C. prior to use. Each flask is inoculated with 2 ml of a seed culture liquid of *Pseudomonas aeruginosa* IFO 3919, which has been previously obtained by seeding said strain in a seed medium (pH 6.4) composed of 1% of glucose, 1.5% of peptone, 0.3% of $K_2HPO_4$ and 0.02% of $MgSO_4.7H_2O$, followed by the incubation thereof. The flask is incubated at 28° C. for 24 hours under aerobic conditions, thereafter the culture broth thus obtained is centrifuged to obtain 45 g of the wet cells. The wet cells are added to 100 ml of 0.01 M potassium phosphate buffer (pH 8.0) containing 10 M 2-mercaptoethanol, disrupted by ultrasonic oscillator and then centrifuged (at 25,000×G) and, as a result 96 ml of supernatant is obtained. This supernatant shows a specific activity of acyl-CoA synthetase of 0.230 μmoles/mg/hour as palmitoyl-CoA synthetase activity.

It will be obvious to those skilled in the art that various changes may be made without departing from the scope of the invention and the invention is not to be considered limited to what is described in the specification.

What is claimed is:

1. A process for preparing acyl-CoA synthetase LCF-18, comprising cultivating *Pseudomonas aeruginosa* IFO 3919 in a medium under aerobic conditions until a substantial amount of acyl-CoA synthetase LCF-18 is accumulated in the cells, and then isolating acyl-CoA synthetase LCF-18 from the thus cultured cells.

* * * * *